United States Patent
Jbach et al.

(10) Patent No.: US 10,661,263 B2
(45) Date of Patent: *May 26, 2020

(54) METHOD FOR CATALYTICALLY PRODUCING FORMIC ACID AND REGENERATING THE CATALYST USED IN THE PROCESS WITH LITTLE OVERPRESSURE

(71) Applicant: OXFA GMBH, Scheßlitz (DE)

(72) Inventors: Hermann Wolf Jbach, Bischberg (DE); Florian Kohler, Nuremberg (DE); Matthias Schmidt, Erlangen (DE); Gunthard Scholz, Gundelsheim (DE)

(73) Assignee: OXFA GmbH, Schesslitz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/318,679

(22) PCT Filed: Jul. 17, 2017

(86) PCT No.: PCT/EP2017/068054
§ 371 (c)(1),
(2) Date: Jan. 17, 2019

(87) PCT Pub. No.: WO2018/015351
PCT Pub. Date: Jan. 25, 2018

(65) Prior Publication Data
US 2019/0291093 A1    Sep. 26, 2019

(30) Foreign Application Priority Data
Jul. 18, 2016   (DE) .................. 10 2016 213 099

(51) Int. Cl.
*B01J 38/58* (2006.01)
*C07C 51/23* (2006.01)
(Continued)

(52) U.S. Cl.
CPC ............ *B01J 38/58* (2013.01); *B01D 53/047* (2013.01); *B01D 53/229* (2013.01);
(Continued)

(58) Field of Classification Search
CPC .......... B01J 38/58; B01J 38/02; B01J 27/285; B01D 53/047; B01D 53/229; C07C 51/23; C07C 51/48; C07C 53/02
See application file for complete search history.

(56) References Cited

U.S. PATENT DOCUMENTS

2013/0245319 A1*  9/2013  Bosmann ................ C07C 51/23
562/531

FOREIGN PATENT DOCUMENTS

| DE | 10 2011 077 232 A1 | 3/2012 |
| DE | 10 2014 212 995 A1 | 1/2016 |
| EP | 2 473 467 B1 | 9/2013 |

OTHER PUBLICATIONS

International Search Report, International Application No. PCT/EP2017/068054 (published under WO 2018/015351), 4 pages (dated Sep. 22, 2017).

* cited by examiner

*Primary Examiner* — Yate' K Cutliff
(74) *Attorney, Agent, or Firm* — Prismatic Law Group, PLLC

(57) ABSTRACT

The invention relates to catalytically producing formic acid and regenerating the catalyst used in the process. A vanadyl ion, vandate ion, or polyoxometallate ion, which is used as the catalyst, of the general formula $[PMo_xV_yO_{40}]^{n-}$ is brought into contact with an alpha hydroxyl aldehyde, an alpha hydroxy carboxylic acid, a carbohydrate, a glycoside, or a polymer, which contains a carbon chain and which comprises at least two OH groups bonded as substituents to the carbon chain as a substituent in a repeating manner
(Continued)

Figure 1:
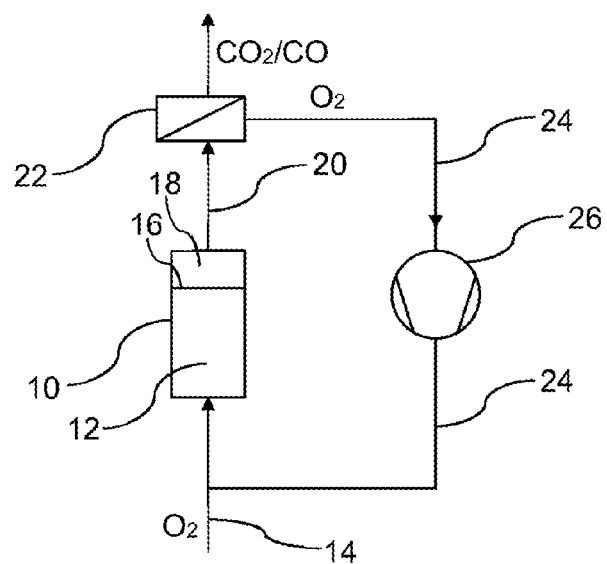

and/or an O, N, or S atom contained in the carbon chain in a repeating manner, in a liquid solution (12) in a vessel (10) at a temperature above 70° C. and below 160° C., wherein $6 \leq x \leq 11$, $1 \leq y \leq 6$, $3 < n < 10$, and $x+y=12$, where n, x, and y is each a whole number.

23 Claims, 3 Drawing Sheets

(51) Int. Cl.
*C07C 53/02* (2006.01)
*B01D 53/047* (2006.01)
*B01D 53/22* (2006.01)
*B01F 3/04* (2006.01)
*B01F 5/04* (2006.01)
*B01F 5/06* (2006.01)
*B01J 27/199* (2006.01)
*B01J 27/28* (2006.01)
*B01J 38/02* (2006.01)

(52) U.S. Cl.
CPC .......... *B01F 3/0446* (2013.01); *B01F 5/0413* (2013.01); *B01F 5/0602* (2013.01); *B01J 27/199* (2013.01); *B01J 27/285* (2013.01); *B01J 38/02* (2013.01); *C07C 51/23* (2013.01); *C07C 53/02* (2013.01); *B01D 2256/12* (2013.01); *B01D 2257/502* (2013.01); *B01D 2257/504* (2013.01); *B01F 2215/0036* (2013.01); *Y02P 20/584* (2015.11)

METHOD FOR CATALYTICALLY PRODUCING FORMIC ACID AND REGENERATING THE CATALYST USED IN THE PROCESS WITH LITTLE OVERPRESSURE

This application is a 371 national phase of International Patent Application No. PCT/EP2017/068054 filed Jul. 17, 2017, which claims priority to German Patent Application No. 10 2016 213 099.4 filed Jul. 18, 2016, the content of each of which applications is incorporated herein by reference.

The invention relates to a method for catalytically producing formic acid and regenerating the catalyst employed. A method of this kind is known from EP 2 473 467 B1. It involves contacting a polyoxometalate ion of the general formula $[PMo_xV_yO_{40}]^{5-}$ serving as catalyst at a temperature below 120° C. with an alpha-hydroxyaldehyde, an alpha-hydroxycarboxylic acid, a carbohydrate or a glycoside in a liquid solution, where $6<x<11$ and $1<y<6$ and $x+y=12$, where x and y are each an integer. The catalyst reduced is returned to its original state by oxidation.

According to DE 10 2011 077 232 A1 and its corresponding EP 2 473 467 B1 it is advantageous if the contacting takes place under an oxygen partial pressure of 1 to 500 bar, more particularly 50 to 75 bar. The higher the oxygen partial pressure, the more rapid the oxidation of the catalyst reduced in the method. A reaction vessel for effective implementation of the method known from EP 2 473 467 B1 must be able to withstand considerable pressure. For such a reaction vessel to be safe, it must have relatively thick walls, and joins between materials within the reaction vessel must satisfy stringent safety requirements. The assurance of safety during implementation of the method is complicated as well, owing to the relatively high pressure during the reaction that is needed for effective oxidation of the catalyst. Implementing the method known from EP 2 473 467 B1 is therefore relatively expensive.

DE 10 2014 212 995 A1 discloses a method for catalytic production of carboxylic acids wherein the catalyst used is a polyoxometalate of the form $H_{3+y}[PMo_xV_yO_{40}]$ and is contacted with a carbonaceous solid fuel in a liquid solution, where $6<y<13$, $1<x<6$ and $x+y=12$, and where x and y are each an integer. The catalyst in this case can be regenerated with an oxygen-containing gas mixture having an oxygen partial pressure of between 0.1 bar and 100 bar. The temperature in the method may be below 150° C. With the method it is possible to generate formic acid or acetic acid. The gas given off during the production of formic acid is removed from the process.

It is an object of the present invention to specify a method which can be carried out efficiently and inexpensively for catalytic production of formic acid and regeneration of the catalyst employed.

The object is achieved by the features of claim 1. Useful embodiments are apparent from the features of claims 2 to 18.

Provided in accordance with the invention is a method for catalytically producing formic acid and regenerating the catalyst employed, where a vanadyl ion, vanadate ion or polyoxometalate ion of the general formula $[PMo_xV_yO_{40}]^{n-}$ serving as catalyst is contacted at a temperature above 70° C., more particularly above 80° C., more particularly above 90° C., and below 160° C., more particularly below 150° C., more particularly below 140° C., more particularly below 130° C., more particularly below 120° C., with a substrate in the form of an alpha-hydroxyaldehyde, an alpha-hydroxycarboxylic acid, a carbohydrate, a glycoside or a polymer containing a carbon chain and having at least one OH group bonded repeatedly as substituent to the carbon chain and/or having an O, N or S atom present repeatedly in the carbon chain, in a liquid solution in a vessel. Here $6 \le x \le 11$ and $1 \le y \le 6$ and $3<n<10$ and $x+y=12$, where n, x and y are each an integer. The catalyst reduced here is returned by oxidation to its original state. For this purpose, the solution is contacted with a gas comprising a volume fraction of at least 18%, more particularly at least 19%, more particularly at least 20%, more particularly at least 30%, more particularly at least 40%, more particularly at least 50%, more particularly at least 70%, more particularly at least 90%, more particularly at least 95%, of oxygen at a pressure of at least 2 bar, more particularly at least 3 bar, more particularly at least 4 bar, more particularly at least 5 bar, more particularly at least 6 bar, more particularly at least 7 bar, more particularly at least 8 bar, more particularly at least 9 bar, more particularly at least 10 bar, more particularly at least 11 bar, more particularly at least 12 bar, more particularly at least 13 bar, and at most 16 bar, more particularly at most 15 bar, more particularly at most 12 bar, more particularly at most 10 bar, more particularly at most 9 bar, more particularly at most 7 bar, more particularly at most 6 bar, by means of a mixing apparatus or via a liquid-impermeable, gas-permeable membrane. That volume fraction of the gas that is not oxygen may comprise nitrogen or consist of nitrogen.

The vanadyl ion, i.e., $VO^{2+}$, may be introduced for example in the form of $VOSO_4$ or $VOPO_4$ as a catalyst into the solution. The vanadate ion, i.e., an oxoanion of vanadium in the +5 oxidation state, may be introduced for example as $VO_4^{3-}$, e.g., in a solution of sodium orthovanadate ($Na_3VO_4$), or as the polymeric $[VO_3]_n^{n-}$, as for example in the form of $NaVO_3$ (sodium metavanadate), as a catalyst into the solution.

CO and/or $CO_2$ formed in the reaction pass(es) from the solution into the gas and is/are taken off in a quantity such that the volume fraction of CO and $CO_2$ together in the gas does not exceed 80%. This may be achieved, for example, by using fresh gas to replace the gas contacting the solution, or at least a part of this gas, permanently or intermittently, no later than on attainment of the CO and/or $CO_2$ volume fraction of 80%; in other words, the gas space contacting the solution is flushed with gas not hitherto contacting the solution. Intermittent replacement by fresh gas may be accomplished by discontinuously replacing a part of the solution-contacting gas or the entirety of the solution-contacting gas with fresh gas. The volume, or the volume supplied per unit time, of the gas supplied, in the case of permanent or discontinuously intermittent replacement of the gas contacting the solution, may be regulated as a function of the measured volume fraction of CO and $CO_2$ together in the gas, more particularly in the gas departing the gas space. Alternatively, CO and/or $CO_2$ formed may be taken off by separating the CO and/or the $CO_2$ from the gas no later than on attainment of this volume fraction of 80%. The "volume fraction of CO and $CO_2$ together" refers to the sum of the volume fractions of CO and $CO_2$. A gas here is taken to mean a gas or a gas mixture. The composition of the gas is subject to continual change in the course of the method, as a result of the formation of CO and/or $CO_2$, as a result of the removal of CO and/or $CO_2$ formed, and by the withdrawal of oxygen as a result of the oxidation of the catalyst, for example. The gas used at the outset and the fresh gas for flushing the solution-contacting gas space may be, for example, air, which typically has an oxygen content of around 20.9 to 21%. Oxygen needed for the method may also be obtained by electrolysis of water. The hydrogen that is formed at the same time in that case may be used by combustion to heat the solution or in another optional step of the method, for example to rectify formic acid that has been formed. The hydrogen may also be used for chemical hydrogenation of $CO_2$ formed in the method, to give formic acid.

The method of the invention may be carried out in relation to the solution and/or the reactant to be converted, i.e., the alpha-hydroxyaldehyde, the alpha-hydroxycarboxylic acid, the carbohydrate, the glycoside or the polymer, as a batch method, as a fed-batch method or as a continuous method, in the vessel or in two or more vessels. In the case of the batch method, no further solution and no further reactant, i.e., no further alpha-hydroxyaldehyde, no further alpha-hydroxycarboxylic acid, no further carbohydrate, no further glycoside, and no further polymer, are added to the solution after the start of the method. The fed-batch method is a method in which the vessel to start with is filled with only part of the solution or part of the reactant to be converted in the method, and in which further solution or further reactant is added in the course of the method, in one or more steps. With the continuous method, the solution initially present in the vessel and the reactant initially present in the vessel is/are supplied permanently with solution and/or with unconsumed reactant, and solution with formic acid produced and optionally consumed reactant is taken off. With the batch method and with the fed-batch method and also with the continuous method, the supply and removal of the gas may take place independently of the supply and the removal of the solution and/or of the reactant, as described above, for example.

In the method, the CO and/or the $CO_2$ may be separated from the gas. Separation may be accomplished, for example, by liquefaction of $CO_2$ by compression, or by means of a membrane which is permeable to $CO_2$ and/or CO but is impermeable or of only limited permeability to oxygen, or by a combination of two or more membranes with different permeabilities—for example, a first membrane which is permeable to $CO_2$ and CO and impermeable or of only limited permeability to $O_2$, and a second membrane which is permeable to $CO_2$ and impermeable or of only limited permeability to CO. Through the combination of membranes with different permeabilities, the separated gas may be deposited separately and then supplied for further use. Alternatively, the CO and/or $CO_2$ may also be separated from the gas by means of pressure swing adsorption. Through separation it is possible to obtain a relatively pure $CO_2$, which can be utilized as a product. The separated $CO_2$ may also be converted into formic acid by means of electrochemical reduction.

In one embodiment of the method, the volume fraction of CO and $CO_2$ together in the gas is at least 20%, more particularly at least 25%, more particularly at least 30%, and/or the CO and/or $CO_2$ formed in the reaction and passing into the gas are/is taken off in a quantity such that the volume fraction of CO and $CO_2$ together in the gas does not exceed 70%, 60%, 55%, 50%, 45%, 40%, 35%, 30%, 25% or 20%. The CO and/or $CO_2$ formed in the reaction and passing into the gas can be taken off in a quantity such that the volume fraction of CO and $CO_2$ together in the gas does not exceed 80%, 70%, 60%, 55%, 50%, 45%, 40%, 35%, 30%, 25% or 20% by using fresh gas to replace the gas contacting the solution, or at least a part of this gas, permanently or intermittently, no later than on attainment of this volume fraction of 80%, 70%, 60%, 55%, 50%, 45%, 40%, 35%, 30%, 25% or 20%, or by separating the CO and/or the $CO_2$ from the gas no later than on attainment of this volume fraction of 80%, 70%, 60%, 55%, 50%, 45%, 40%, 35%, 30%, 25% or 20%. Fresh gas is gas which up to that point has not contacted the solution, has an oxygen content of at least 18%, and has a combined volume fraction of CO and $CO_2$ that is lower than that of the gas replaced. For a volume fraction of CO and $CO_2$ together of at most 80%, the minimum volume fraction of oxygen can be 20% if no further gas is otherwise present. Accordingly, the minimum volume fraction of oxygen in the case of a volume fraction of CO and $CO_2$ together of at most 70%, 60%, 55%, 50%, 45%, 40%, 35%, 30%, 25% or 20% can be in each case 30%, 40%, 45%, 50%, 55%, 60%, 65%, 70%, 75% or 80% if no further gas is otherwise present. The stated volume fraction of CO and $CO_2$ together in the gas of at least 20%, more particularly at least 25%, more particularly at least 30%, has proven economically to be favorable if the rest of the volume fraction consists largely of oxygen, because the enriched oxygen is relatively expensive and, particularly when separating CO and $CO_2$ via a membrane, there is always the risk of a loss of part of the oxygen.

The catalyst reduced during the reaction to form the formic acid is returned to its original state by oxidation. In the context of the invention, therefore, a catalyst also comprehends a substance which is altered by reduction during the method and is returned to its original state by oxidation.

The liquid solution may be an aqueous solution. The solution refers to a solution of the catalyst. The substrate and other constituents may be dissolved therein or else just present therein in suspension. The solution may comprise a solvent for dissolving the substrate. The provision of such a solvent is not necessary if the alpha-hydroxyaldehyde, the alpha-hydroxycarboxylic acid, the carbohydrate, the glycoside or the polymer is already in liquid form. In that case the liquid solution may also be a solution of the catalyst in the substrate. An alpha-hydroxyaldehyde is any molecule in which an OH group is bonded directly to a carbon atom, the carbon atom also having a direct bond to the carbon atom of an aldehyde group. An alpha-hydroxycarboxylic acid is any molecule in which an OH group is bonded directly to a carbon atom, the carbon atom also having a direct bond to the carbon atom of a carboxyl group. An alpha-hydroxyaldehyde and an alpha-hydroxycarboxylic acid may also be taken to be any substance which comprises an alpha-hydroxyaldehyde or an alpha-hydroxycarboxylic acid.

The inventors of the present patent application have ascertained that the CO and/or $CO_2$ formed in the catalytic conversion of the stated substrates under a limited pressure has/have an unexpectedly strongly limiting effect on the yield of formic acid and/or on the rate of production of formic acid. They have further ascertained that by minimizing the volume fraction of CO and $CO_2$ together in the gas, so that the volume fraction does not exceed 80%, 70%, 60%, 55%, 50%, 45%, 40%, 35%, 30%, 25% or 20%, it is possible on the one hand to boost the yield and/or the rate of formation of formic acid and on the other hand to carry out the method with a relatively low pressure of not more than 16 bar, or even not more than 15 bar, or even not more than 12 bar, or even not more than 10 bar, or even not more than 9 bar, or even not more than 8 bar, or even not more than 7 bar, or even not more than 6 bar, with sufficient yield and/or rate of formation of formic acid and/or with sufficient specific product yield (space-time yield). The method, indeed, makes it possible to carry out the oxidation of the catalyst with air at the aforementioned pressure with sufficient efficiency. Since, as a result, the apparatus for implementing the method is required to withstand a lower pressure, the apparatus can be provided at much more favorable cost than an apparatus for implementing the method known from EP 2 473 467 B1 for the catalytic production of formic acid.

In one embodiment of the method, the volume fraction of the oxygen in the gas contacting the solution is at least 45%, more particularly at least 50%, more particularly at least 60%, more particularly at least 70%, more particularly at least 80%, more particularly at least 85%, more particularly at least 90%, more particularly at least 95%, more particularly at least 96%, more particularly at least 98%, more particularly 100%. The gas pressure may be at least 6 bar, more particularly at least 7 bar, more particularly at least 8 bar, more particularly at least 9 bar, more particularly at least 10 bar, more particularly at least 11 bar, more particularly at least 12 bar, more particularly at least 13 bar. In one embodiment of the method, the gas pressure of the gas is at most 15 bar, more particularly at most 12 bar, more particularly at most 10 bar, more particularly at most 9 bar, more particularly at most 8 bar, more particularly at most 7 bar, more particularly at most 6 bar. The method of the invention can also be carried out such that the partial pressure of CO and $CO_2$ together at an interface of the solution with the gas does not exceed 13 bar, more particularly 12 bar, more particularly 10 bar, more particularly 5 bar, more particularly 2 bar, more particularly 1 bar. The "partial pressure of CO and $CO_2$ together" refers to the sum of the partial pressures of CO and $CO_2$. The efficiency of the method can be boosted by lowering the partial pressure of CO and/or $CO_2$ or of CO and $CO_2$ together.

The CO and/or $CO_2$ formed in the reaction and passing into the gas may be taken off in a quantity such that, with a pressure restricted to a maximum value or with pressure held constant, the oxygen partial pressure in the gas is diminished by the CO and/or $CO_2$ by not more than 10%, more particularly not more than 8%, more particularly not more than 6%, more particularly not more than 4%, more particularly not more than 2%, more particularly not more than 1%. Depending on the substrate, in particular on the ratio of carbon to hydrogen in the substrate and the concentration of the substrate, a greater or lesser amount of CO and/or $CO_2$ may be formed during the production of formic acid. There is usually always more $CO_2$ formed than CO, with the ratio of $CO_2$ formed to CO formed likewise being dependent on the substrate but also on the process conditions. Customarily the ratio of $CO_2$ formed to CO formed is between 3:1 and 20:1. Because the oxygen partial pressure is kept constant or at least relatively constant, by regulation of the quantity of CO and/or $CO_2$ to be taken off, by flushing with fresh gas, for example, as a function of the oxygen partial pressure, it is possible to keep the oxygen partial pressure within a range that is favorable for the process. By means of said regulation, the method can be adapted to different substrates and substrate concentration. As a result, the catalytic production of formic acid can always take place with the maximum possible efficiency or at least with relatively high efficiency.

For the oxidation of the catalyst, a portion of the liquid solution may be led out of the vessel, contacted with the gas, and subsequently supplied again to the remainder of the liquid solution. The portion of the liquid solution may be supplied at overpressure to the remainder of liquid solution. Here, oxygen dissolved therein may also contribute to oxidation of a portion of the catalyst present in the remainder of the liquid solution.

The supplying of the portion of the liquid solution that is under a higher pressure relative to the remainder of the liquid solution to the remainder of the liquid solution under this pressure may also be configured, owing to the pressure difference between the portion and the remainder of the liquid solution, as an inflowing of the portion into the remainder of the liquid solution, and may be utilized for commixing of the liquid solution and for dispersion of the gas in the liquid solution. The inflowing may take place via at least one correspondingly configured nozzle, which in particular is variable in terms of the direction of flow and/or in its outlet diameter. By changing the outlet diameter it is possible to modify the outflow velocity of the portion of the liquid solution from the nozzle.

In order to take off the CO and/or $CO_2$ when the stated volume fraction is exceeded, the vessel may have an outward-leading opening which is regulated by a valve. To prevent formic acid that has been formed being lost in vapor form, a condensing apparatus may be provided on the vessel or outside the vessel, allowing formic acid vapor formed, in particular prior to the replacement of the solution-contacting gas with fresh gas, to condense, optionally together with water, and so a condensate produced by this means can be led back into the vessel, supplied to an extraction in order to separate the formic acid from the water contained therein, or can be led off for the purpose of separation of the formic acid. It is advantageous in this case that the catalyst does not vaporize at the temperature of the method, hence allowing the formic acid to be recovered without any need for separation of the formic acid from the catalyst. Alternatively, vaporous formic acid formed in the gas may be absorbed from the gas or from the aforementioned condensate, more particularly before the replacement of the solution-contacting gas by fresh gas, by means of an absorbent suitable for absorbing formic acid, more particularly a linear alcohol, more particularly 1-pentanol, 1-hexanol, 1-heptanol, 1-octanol or 1-decanol, or an amide, more particularly an N,N-dialkylcarboxamide, more particularly dipentylformamide, N-(n-hexadecyl)formamide, N,N-di-n-butylformamide (DBFA), N-di-n-acetamide, N-methyl-N-heptylformamide, N-n-butyl-N-2-ethylhexylformamide or N-n-butyl-N-cyclohexylformamide, and subsequently desorbed therefrom. The desorbing may be brought about, for example, by flash vaporization, i.e., by vaporization through lowering of the pressure. The absorbent thereafter can be brought back by means of a heat exchanger to a desired temperature suitable for the absorption, and used again for the absorption.

It is also possible for the formic acid to be absorbed from the gas by a base, more particularly an aqueous solution of NaOH or KOH, and for the salt solution resulting from this to be led off for further use.

The portion of the liquid solution may be led off from the vessel continuously or at intervals, more particularly at regular intervals, and may be subjected to the gas at a pressure of at least 2 bar, 3 bar, 4 bar or 5 bar and at most 16 bar, and then supplied again to the remainder of the liquid solution, continuously or at intervals, more particularly at regular intervals.

The oxidizing as well may be carried out continuously or at intervals, more particularly at regular intervals. This makes it possible to provide the catalyst present in the vessel in a sufficient quantity, throughout the method, in an oxidized form which is therefore suitable for the reaction of the alpha-hydroxyaldehyde, the alpha-hydroxycarboxylic acid, the carbohydrate, the glycoside or the polymer, without any need for this purpose to use too great a quantity of the relatively expensive catalyst.

In the embodiment of the method wherein the catalyst is oxidized by a portion of the liquid solution being led off from the vessel, then contacted with the gas, and subsequently returned to the remainder of the liquid solution, the portion of the liquid solution may be maintained at constant or at least virtually constant temperature by means, for example, of a heat exchanger.

To prevent coarse solids passing into that part of the apparatus for implementing the method that is situated downstream in the direction of flow, where they could block valves or other parts of the apparatus, for example, or otherwise impair them in their functioning, it is possible to provide—when leading out the portion of the liquid solution from the vessel—a hydrocyclone, a decanter or a filter, more particularly a countercurrent filter, a microfilter or an ultrafilter.

In one embodiment of the method of the invention, the alpha-hydroxyaldehyde, the alpha-hydroxycarboxylic acid, the carbohydrate, the glycoside or the polymer is present in the liquid solution in the form of solids dispersed therein. The solids may be in fine dispersion or coarse dispersion in the liquid solution.

The polymer may be a polyester, a polyamine or a polyamide, more particularly polyhexamethyleneadipamide (nylon). The polymer may be a polymer without plasticizers. Plasticizers may adversely affect the activity of the catalyst.

Alpha-hydroxyaldehydes, alpha-hydroxycarboxylic acids, carbohydrates, and glycosides occur in a large number of renewable raw materials, such as starch, cellulose or hemicellulose, for example. Starch, cellulose, and hemicellulose are obtained in large quantities as a product from field plants or in the industrial pulping of wood, for papermaking, for example.

The alpha-hydroxyaldehyde, the alpha-hydroxycarboxylic acid, the carbohydrate or the glycoside may be a monosaccharide, more particularly an aldose, disaccharide, oligosaccharide or polysaccharide, starch, cellulose, hemicellulose, glucose, sucrose, xylose, cellobiose, xylan, a heterooligosaccharide, a heteropolysaccharide, glycolic acid or lactic acid, or a residual material or raw material, more particularly renewable raw material, more particularly untreated raw material, that comprises the alpha-hydroxyaldehyde, the alpha-hydroxycarboxylic acid, the carbohydrate or the glycoside. Untreated here means that the raw material has not been subject to chemical digestion beforehand. The residual material or the renewable raw material may be a plant, a fungus or bacteria, or constituents of plants, fungi or bacteria; wood, more particularly in the form of wood flour or wood chips, paper, especially waste paper; algae, cyanobacteria, silage, or a protein-rich substance, more particularly spent distillery grains, marc, or spent brewery grains. The alpha-hydroxyaldehyde, the alpha-hydroxycarboxylic acid, the carbohydrate or the glycoside may also comprise a mixture of at least two of the stated substances or may have been formed from at least one of the stated substances or from the mixture, as is the case, for example, with brown coal or peat.

Many of the stated raw materials are obtained as byproducts, in papermaking or wood processing, for example. They are therefore available as a favorable starting material for the method of the invention. As a result, the method of the invention can be carried out very cost-effectively. Another contributor to this is the oxidation of the catalyst reduced in the catalyzed reaction (i.e., reoxidation), which allows the catalyst to be used for a very long time.

The mixing apparatus may comprise a static mixer, a reactive mixing pump, a nozzle, more particularly a Venturi nozzle or a spraying nozzle, and/or a gas introduction stirrer. For this purpose, the mixing apparatus may consist of at least one of the stated mixing means or may comprise a plurality thereof or else a plurality of different mixing means from among those stated. The mixing apparatus may be configured and operated, or the membrane constructed, in such a way as to increase the surface area of the solution, i.e., the interface between the solution and the gas, by a factor of at least 1000, more particularly by a factor of at least 5000, more particularly by a factor of at least 10 000. The size of this factor is frequently dependent, according to mixing apparatus, not only on the mixing apparatus itself but also on the nature of its operation, such as the stirring speed in the case of a gas introduction stirrer, the rotary speed in the case of a reactive mixing pump, or the flow rate in the case of a static mixer, a Venturi nozzle or a spraying nozzle.

The separation of $CO$ and/or $CO_2$ makes it possible for the gas to be circulated, in particular without a pressure drop of more than 2.5 bar, more particularly more than 2 bar, more particularly more than 1.5 bar, more particularly more than 1 bar, more particularly more than 0.5 bar, by means of a conveying apparatus, such as a compressor, a Venturi nozzle or a fan. As a result, it is also possible to maintain a higher oxygen content in the gas than in air, without oxygen, or at least a substantial quantity of oxygen, escaping from the circuit, except through oxidation of the catalyst. A relatively high oxygen content in the gas raises the efficiency of the oxidation of the catalyst by comparison with a gas having a lower oxygen content, such as air, for example.

In the case of one embodiment, the overall method is carried out as a continuous process. For this purpose, for example, continuously or at intervals, more particularly at regular intervals, a portion of the liquid solution can be led off from the vessel, and formic acid contained in this portion, in the form of a formate, for example, can be separated, and the remaining portion of the liquid solution can be returned to the remainder of the liquid solution. One method suitable for this purpose is described in WO 2016/078698 A1, for example.

The catalyst and the formic acid can be separated from the solution, or from a portion of the solution that is subsequently resupplied to the solution, by means of at least one extractant, more particularly with the pH being maintained at not more than 3, more particularly not more than 2.5, more particularly not more than 2, in the solution. Maintaining the pH at not more than 3, more particularly not more than 2.5, more particularly not more than 2 can be achieved by extracting only a part of the formic acid from the solution or from the portion of the solution, and leaving enough formic acid in the solution so that the pH does not rise above 3, more particularly not above 2.5, more particularly not above 2. The extractant for the catalyst and the formic acid may be identical. It may in particular be a polar organic extractant which extracts the formic acid and the catalyst and which on mixing with the liquid solution forms a phase boundary between the solution and the extractant. The extractant may be an extractant which, for extracting the catalyst present at a concentration of 1.5 wt % in water, has a partition coefficient for the catalyst at 40° C. that is greater by a factor of at least 7, more particularly 8, more particularly 9, more particularly 10, more particularly 15, more particularly 20, more particularly 25, more particularly 30 than a partition coefficient for extraction of the formic acid present at a concentration of 5 wt % in water at 40° C. The partition coefficient K is defined as follows:

K+(concentration of formic acid or catalyst) in the extractant/(concentration of formic acid or catalyst) in the water The extractant may as a result extract the catalyst at the start of the extraction more rapidly than the formic acid. "More rapidly" here means in particular that a greater weight percentage of the catalyst, as a proportion of the total catalyst present in the solution, passes into the extractant per unit time than of the formic acid as a proportion of the total formic acid present in the solution.

To retain solids dispersed in the liquid within the vessel, it is possible, when leading out the portion of the liquid solution from the vessel, to provide a hydrocyclone, a decanter or a filter, as for example a countercurrent filter, a microfilter or an ultrafilter.

The extractant may be saturated with the catalyst before the extraction, or the separated catalyst may be separated from the extractant and supplied to the liquid solution in the vessel. This prevents the concentration of the catalyst in the vessel falling to such an extent that efficient production of the formic acid is no longer possible.

The separation may take place in a two-stage process, by extracting the solution in a first extraction step with a first quantity of the extractant for a first time, to extract the catalyst, and extracting the solution in a second extraction step with a second quantity of the extractant for a second time, to extract the formic acid. The catalyst extracted in the first extraction step may be passed back to the liquid solution in the vessel. The extractant may for example be an amide, more particularly an N,N-dialkylcarboxamide, more particularly dipentylformamide, N-(n-hexadecyl)formamide, N,N-di-n-butylformamide (DBFA), N-di-n-acetamide, N-methyl-N-heptylformamide, N-n-butyl-N-2-ethylhexylformamide or N-n-butyl-N-cyclohexylformamide. In the case of the extraction of a solution containing aqueous formic acid and the catalyst, and in the case of brief extraction with relatively little of such an extractant, it is initially primarily the catalyst and only minimally formic acid that are extracted. In the case of a subsequent extraction with the same extractant, it is then primarily formic acid that is extracted from the solution. To prevent formic acid being extracted from the solution in the first extraction stage, the extractant may be saturated beforehand with formic acid. The extractant may be admixed with an additive, more particularly an apolar additive. The apolar additive may be, for example, petroleum, a fraction of petroleum, n-hexane, n-octane, n-decane, oleyl alcohol, toluene, dibutyl ether or tri-n-butyl phosphate.

The catalyst may be separated by means of precipitation as a salt, in particular simultaneously with a precipitation of extracted formic acid as formate, or by means of a further extraction with a polar further extractant, more particularly a solvent of the solution, and with a temperature change of the extractant and/or with an increase in the pH of the extractant, more particularly through addition of a carbonate, sodium carbonate for example. The pH may alternatively or additionally also be increased by addition of a hydroxide, KOH or NaOH for example. The further extractant may, for example, be water or the solution in which the formic acid is produced. The extraction by the further extractant, and the temperature change and/or the increase in pH, may be promoted by the apolar additive. In the case of precipitation of the catalyst, formates may also be coprecipitated at the same time. In such an event, it will be necessary to carry out subsequent separation of the catalyst from the formates, by means of a further extraction step, for example. Before being passed back to the solution, the precipitated catalyst may be dissolved in an acidified aqueous solution, more particularly in an aqueous solution acidified with formic acid. The acidification allows the pH to be adapted to the pH of the solution. This may prevent the pH of the solution changing as a result of the dissolved catalyst being added.

The extracted formic acid may be separated from the extractant by precipitation as a formate or by distillation. In the case of distillation, a so-called flash distillation may be used. Such a distillation is just a single-stage operation and is therefore very straightforward.

Figure 2:
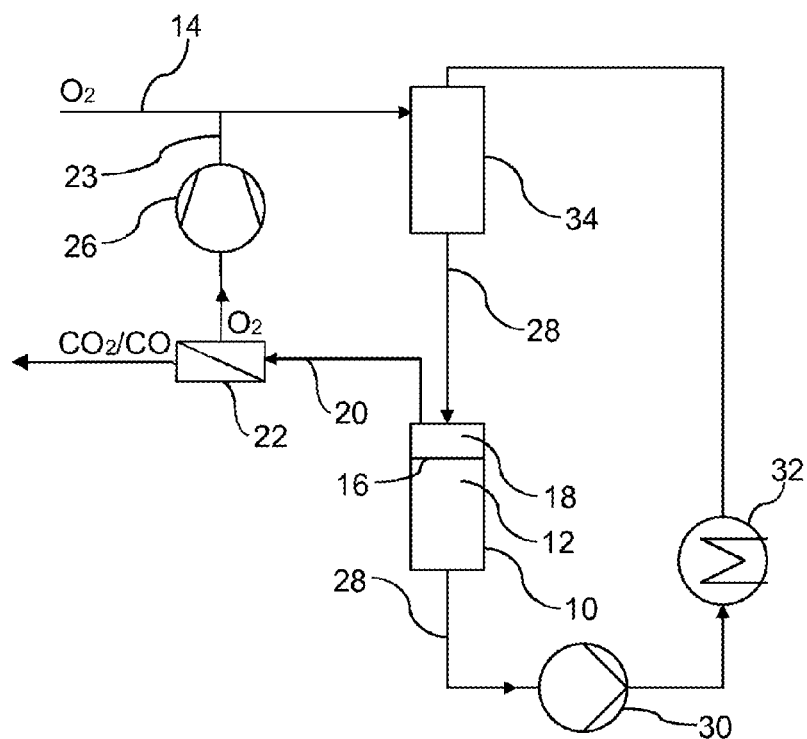
Figure 3:
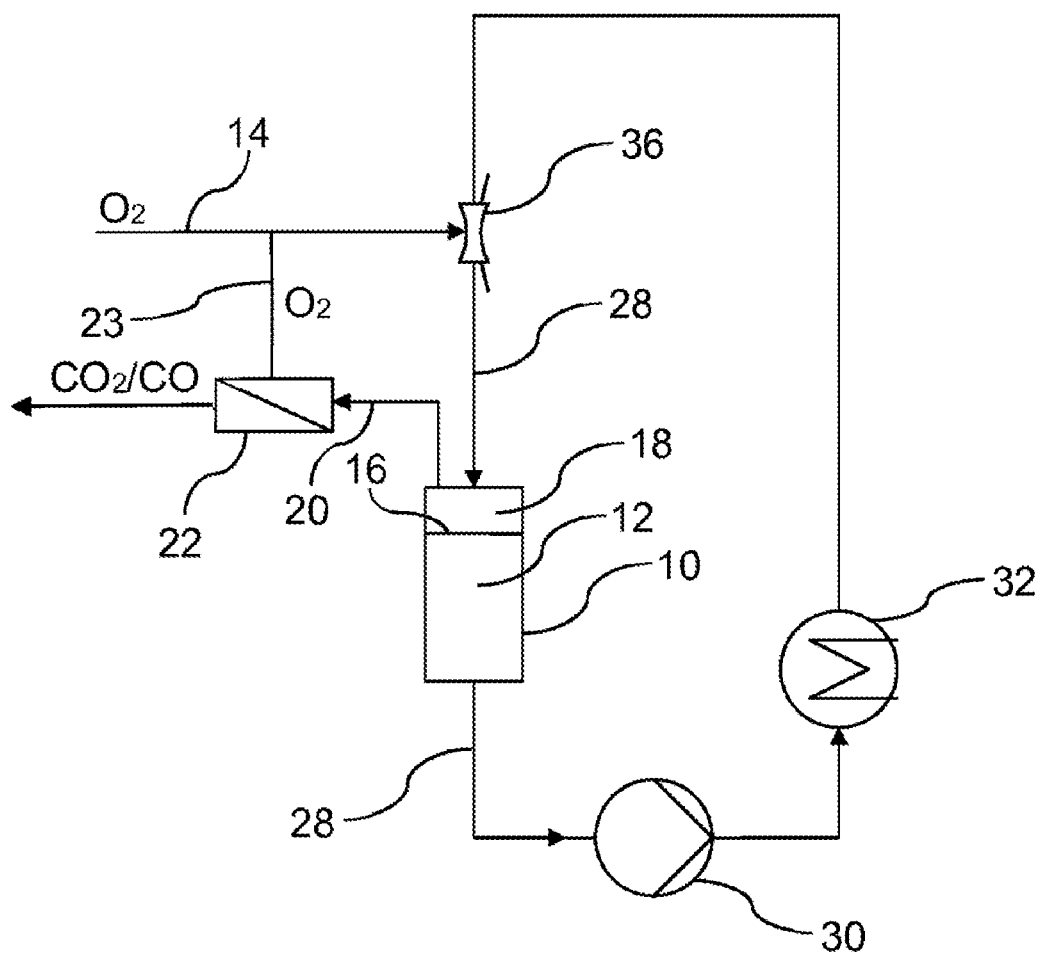
Figure 4:
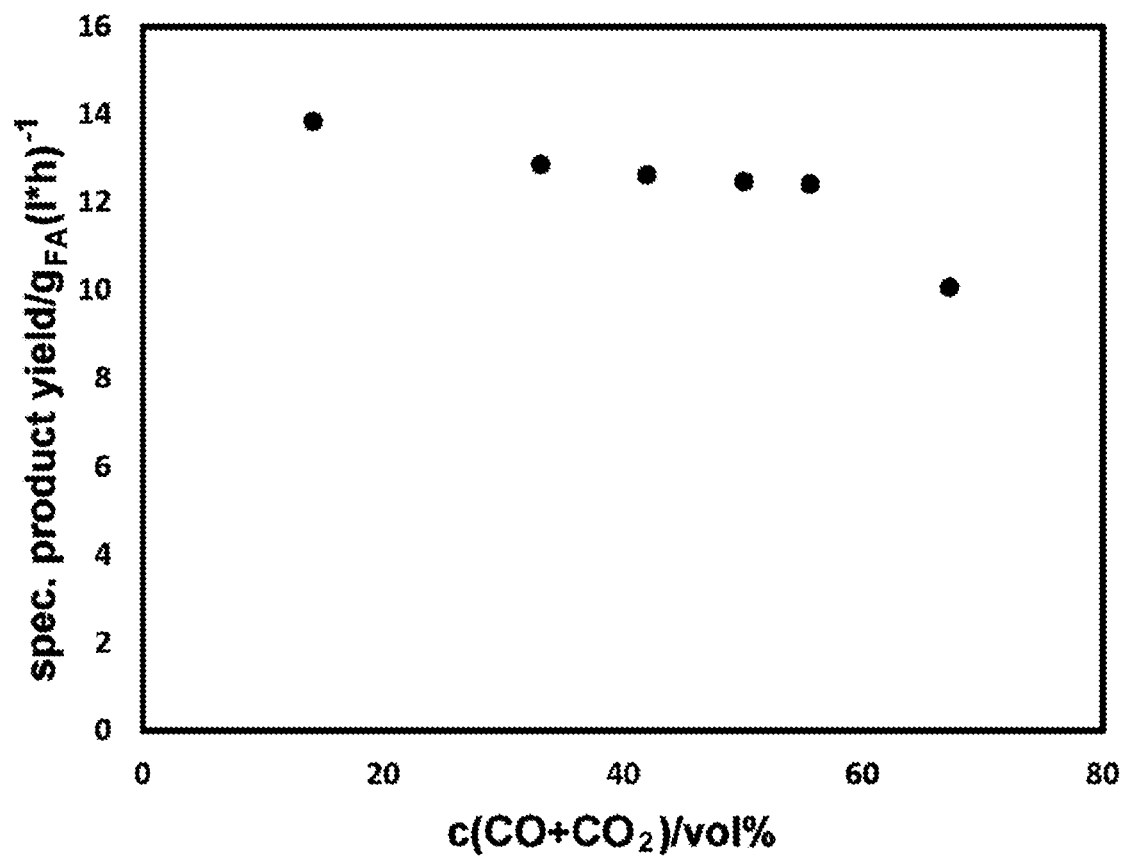

The invention is elucidated in more detail below using exemplary embodiments. In the drawings:

FIG. 1 shows a schematic representation of an apparatus for implementing the method of the invention, FIG. 2 shows a schematic representation of an alternative apparatus for implementing the method of the invention, with a static mixer, FIG. 3 shows a schematic representation of an alternative apparatus for implementing the method of the invention, with a Venturi nozzle, and FIG. 4 shows a graphic representation of the yield of formic acid as a function of the volume fraction of CO and $CO_2$ together in the gas.

FIG. 1 shows a vessel 10 which contains the solution 12 with the catalyst and with a substrate in the form of an alpha-hydroxyaldehyde, an alpha-hydroxycarboxylic acid, a carbohydrate, a glycoside or a polymer containing a carbon chain and having at least one OH group bonded repeatedly as substituent to the carbon chain and/or having an O, N or S atom present repeatedly in the carbon chain.

Opening into the vessel 10 is the supply line 14 for supplying the gas 18 comprising a volume fraction of at least 18% of oxygen. The gas 18 may be supplied from outside or via the return line 24 described below. The surface of the solution 12 forms the interface 16 with the gas 18, this gas collecting in the vessel 10 above the solution 12 and exhibiting a gas pressure of at least 5 bar and at most 33 bar. The gas is supplied to the separator 22 via the offtake line 20. In the separator 22 there is a separation of CO and/or $CO_2$ from the gas by means of a membrane which is permeable to CO and $CO_2$ but impermeable or of only limited permeability to $O_2$, or by means of pressure swing adsorption. The remaining gas is fed back into the supply line 14, via the return line 24 and the compressor 26, before being blown back into the solution 12. The oxygen in the gas that is not consumed by oxidation of the catalyst is circulated accordingly, while the CO and/or $CO_2$ formed in the solution during the reaction are/is separated.

FIG. 2 shows an alternative apparatus which allows the method of the invention to be implemented with a greater efficiency than the apparatus shown in FIG. 1. The solution 12 of the aforementioned substrate, present in the vessel 10, is led out of the vessel 10 through the liquid line 28 and is pumped by means of the pump 30 first through the heat exchanger 32 and then through the static mixer 34. The static mixer 34 is supplied via the supply line 14 with a gas comprising a volume fraction of at least 18% of oxygen and having a gas pressure of at least 5 bar and at most 33 bar, from the outside or from the feed line 23, described below, and said gas is contacted with the solution 12 in the static mixer 34 under this pressure. This is accompanied by a large increase in the surface area of the solution 12 and hence an increase in the interface 16 with the gas 18, and consequently by effective oxidation of the catalyst. By means of the heat exchanger 32, the solution 12 is kept at a constant temperature.

After passing through the static mixer 34, the solution 12 with the gas 18 dispersed therein in small bubbles is introduced through the liquid line 28 into the vessel 10 and is jetted into the solution 12. The effect of this, in addition to the intense commixing which takes place in the static mixer 34, is a further intense commixing of the solution 12 with the gas 18, and so as a result of this as well there is oxidation of the catalyst in the vessel 10. The gas 18 under pressure over the solution 12 is supplied via the offtake line 20 to the separator 22, in which $CO_2$ and/or CO are/is separated from the gas 18 by means of a membrane or pressure swing adsorption. The gas 18 is then fed via a compressor 26 and the feed line 23 into the supply line 14, from where it is fed into the static mixer 34. The compressor 26 conveys the pressurized gas 18 within the circuit thus formed. The oxygen in the gas 18 that is not needed for the oxidation of the catalyst is circulated in this way, while the CO and/or $CO_2$ formed by the reaction are/is separated in the separator 22. This prevents the volume fraction of CO and $CO_2$ together in the gas exceeding 55%.

The apparatus shown in FIG. 3 differs from the apparatus shown in FIG. 2 in that, rather than the static mixer 34, there is a Venturi nozzle 36. The solution 12 supplied to the Venturi nozzle 36 via the liquid line 28 flows through the Venturi nozzle 36, entraining, as it does so, the gas 18 supplied via the supply line 14, as a result of the Venturi effect. The Venturi nozzle 36 brings about intense commixing of the gas 18 with the solution 12. Further intense commixing with the solution 12 is brought about by the jetting of the solution 12, with the gas 18 dispersed therein as small bubbles, from the Venturi nozzle 36 into the solution 12 in the vessel 10. The solution 12 may be jetted via the liquid line 28. Also possible, however, is for the Venturi nozzle 36 to be disposed directly on the vessel 10 and for the solution 12 to be jetted directly from the Venturi nozzle 36 into the solution 12.

Because the Venturi nozzle 36 conveys the gas 18 in a circuit, there is no need here for a compressor 26. The provision of the Venturi nozzle 36 simplifies the apparatus and so makes it more cost-effective. It is also possible to lead the solution 12 first through a static mixer 34 and then through a Venturi nozzle 36, or initially through a Venturi nozzle 36 and then through a static mixer 34, and to supply the gas 18, by means of a divided supply line 14, both to the static mixer 34 and to the Venturi nozzle 36. In this case as well, there may be no need for a compressor 26.

FIG. 4 shows the outcome of the determination of the yield of formic acid when using sugar as the reactant in the method of the invention, for different defined volume fractions of CO and $CO_2$ together in the gas. The yield in this case is reported as the specific product yield (space-time yield). Here it is found that in the case of this substrate, the yield of formic acid drops significantly at and above a volume fraction of CO and $CO_2$ together of 55%. Depending on the substrate, this drop may also take place at a lower or higher volume fraction. The highest volume fraction at which the drop takes place is 80%.

Oxidation of a Fermentation Residue 2800 g of an aqueous solution 12 containing 21 g of $H_8PMo_7V_5O_{40}$ and 50.6 g of $H_2SO_4$ are admixed with 195 g of separated fermentation residue (dry matter) from a biogas plant. In a stirred tank autoclave, the solution 12 is contacted with oxygen under an oxygen partial pressure of 4 bar and is stirred at 130° C. For the supply of $O_2$ and removal of resultant $CO_2$, flushing takes place with a gas stream of 0.7 In $O_2$ per minute. After a reaction time of just 5.5 hours, the formic acid content of the reaction solution already corresponds to a yield of approximately 24%.

Oxidation of Spent Distillery Grains

The reaction is carried out as for the oxidation of the fermentation residue. In deviation from that procedure, 98 g of toluenesulfonic acid instead of $H_2SO_4$, and 195 g of dry spent grains from a bioethanol production facility, instead of the fermentation residue, are used. In further deviation, the solution 12 is contacted with oxygen under an oxygen partial pressure of 8 bar. After a reaction time of only 2 hours, the formic acid content of the reaction solution corresponds to a yield of approximately 51%.

Oxidation of Cattle Manure

The reaction is carried out as for the oxidation of the fermentation residue. In deviation from that procedure, 195 g of cattle manure (dry matter), instead of the fermentation residue, are used. In further deviation, the temperature is raised after one hour from 110° C. to 120° C. and after a further 2 hours to 130° C. After a reaction time of 4 hours, the formic acid content of the reaction solution corresponds to a yield of approximately 23%.

Oxidation of Banana Skins 2400 g of an aqueous solution 12 comprising 43.7 g of $H_8PMo_7V_5O_{40}$ and 82.7 g of toluenesulfonic acid are admixed with 90 g of dried banana skin. In a stirred tank autoclave, the solution 12 is contacted with oxygen under an oxygen partial pressure of 10 bar and is stirred at 90° C. To supply $O_2$ and remove resultant $CO_2$, flushing takes place with a gas stream of 1.0 In $O_2$ per minute. After a reaction time of 5 hours in batch operation, the formic acid content of the solution 12 corresponds to a yield of approximately 36%.

Oxidation of Fruit Marc

The reaction is carried out as for the oxidation of the banana skins. In deviation from that procedure, 90 g of dried marc are used instead of the banana skins. After a reaction time of 5 hours in batch operation, the formic acid content of the solution 12 corresponds to a yield of approximately 25%.

Oxidation of Sucrose without Gas Exchange

The reaction is carried out like the oxidation of the fermentation residue. In deviation therefrom, 1652 g of water, 3 g of $H_8PMo_7V_5O_{40}$, 5.7 g of toluenesulfonic acid and 200 g of sucrose are used. In further deviation, the solution 12 is contacted with oxygen under an oxygen partial pressure of 10 bar, without any gas exchange during the reaction, and is stirred at 90° C. After a reaction time of 4 hours, the formic acid content of the reaction solution corresponds to a yield of approximately 30%.

Oxidation of Sucrose with Permanent $O_2$ Stream

The reaction is carried out like the oxidation of the fermentation residue. In deviation procedure, 1652 g of water, 3 g of $H_8PMo_7V_5O_{40}$, 5.7 g of toluenesulfonic acid and 200 g of sucrose are used. In further deviation, the solution 12 is contacted with oxygen under an oxygen partial pressure of 10 bar and is stirred at 90° C. To supply $O_2$ and remove resultant $CO_2$, flushing takes place with a gas stream of 5 In $O_2$ per minute. After a reaction time of 4 hours, the formic acid content of the reaction solution corresponds to a yield of approximately 40%.

LIST OF REFERENCE NUMERALS 10 vessel
12 Solution
14 supply line
16 interface 18 gas
20 offtake line
22 separator
23 feed line
24 return line
26 compressor
28 liquid line
30 pump
32 heat exchanger
34 static mixer
36 Venturi nozzle

The invention claimed is:

1. A method for catalytically producing formic acid and regenerating the catalyst employed, where a vanadyl ion, vanadate ion or polyoxometalate ion of the general formula $[PMo_xV_yO_{40}]^{n-}$ serving as catalyst is contacted at a temperature above 70° C. and below 160° C. with an alpha-hydroxyaldehyde, an alpha-hydroxycarboxylic acid, a carbohydrate, a glycoside or a polymer containing a carbon chain and having at least two OH groups bonded as substituents to the carbon chain and/or having an O, N or S atom present repeatedly in the carbon chain, in a liquid solution in a vessel, where $6 \leq x \leq 11$ and $1 \leq y \leq 6$ and $3 < n < 10$ and $x+y=12$, where n, x and y are each an integer, where the catalyst reduced is returned by oxidation to its original state, characterized in that the liquid solution for this purpose is contacted with a gas comprising a volume fraction of at least 18% of oxygen at a pressure in a range of 2 to 16 bar, by means of a mixing apparatus or via a liquid-impermeable, gas-permeable membrane, where CO and/or $CO_2$ formed in the reaction and passing into the gas are/is taken off in a quantity such that the volume fraction of CO and $CO_2$ together in the gas does not exceed 80%.

2. The method as claimed in claim 1, characterized in that the volume fraction of CO and $CO_2$ together in the gas is at least 20% and/or in that the CO and/or $CO_2$ formed in the reaction and passing into the gas are/is taken off in a quantity such that the volume fraction of CO and $CO_2$ together in the gas does not exceed 70%.

3. The method as claimed in claim 1, characterized in that the CO and/or $CO_2$ formed in the reaction and passing into the gas are/is taken off in a quantity such that the volume fraction of CO and $CO_2$ together in the gas does not exceed 80% by using fresh gas to replace the gas contacting the solution, or at least a part of this gas, permanently or intermittently, no later than on attainment of the volume fraction of 80%, or by separating the CO and/or the $CO_2$ from the gas.

4. The method as claimed in claim 1, characterized in that the vanadyl ion, vanadate ion or polyoxometalate ion is contacted at a temperature above 80° C., with the alpha-hydroxyaldehyde, the alpha-hydroxycarboxylic acid, the carbohydrate, the glycoside or the polymer.

5. The method as claimed in claim 1, characterized in that the pressure is at least 3 bar.

6. The method as claimed in claim 1, characterized in that the CO and/or $CO_2$ formed in the reaction and passing into the gas are/is taken off in a quantity such that, with a pressure restricted to a maximum value or with pressure held constant, the oxygen partial pressure in the gas is diminished by the CO and/or $CO_2$ by not more than 10%.

7. The method as claimed in claim 1, characterized in that for the oxidation of the catalyst, a portion of the liquid solution is led out of the vessel, contacted with the gas, and subsequently supplied again to the remainder of the liquid solution.

8. The method as claimed in claim 1, characterized in that vaporous formic acid formed in the gas is absorbed from the gas by means of an absorbent suitable for absorbing formic acid, or an amide and is subsequently desorbed therefrom, or is absorbed from the gas by a base and the resulting salt solution is led off or is condensed at the vessel or outside the vessel, where a condensate formed as a result is led back into the vessel, supplied to an extraction to separate the formic acid from the water contained therein, or led off for the separation of the formic acid.

9. The method as claimed in claim 1, characterized in that the mixing apparatus comprises a static mixer, a reactive mixing pump, a nozzle and/or a gas introduction stirrer.

10. The method as claimed in claim 1, where the mixing apparatus is designed in such a way and operated in such a way, or the membrane is constructed in such a way, that the surface area of the solution is increased by a factor of at least 1000 as a result.

11. The method as claimed in claim 1, characterized in that the CO and/or the $CO_2$ are/is separated from the gas by means of a membrane which is permeable for the CO and/or the $CO_2$ and impermeable or of only limited permeability for $O_2$, a combination of two or more membranes with different permeabilities, or by means of a pressure swing adsorption.

12. The method as claimed in claim 1, characterized in that the gas is guided in a circuit.

13. The method as claimed in claim 1, characterized in that the method is carried out as a continuous process.

14. The method as claimed in claim 1, characterized in that the catalyst and the formic acid are separated from the liquid solution or from a portion of the liquid solution that is subsequently resupplied to the liquid solution, by means of at least one polar organic extractant which extracts the formic acid and the catalyst and which, on mixing with the liquid solution, forms a phase boundary between the liquid solution and the extractant, in the liquid solution, where the extractant is one which, for extraction of the catalyst present at a concentration of 1.5 wt % in water, has a partition coefficient for the catalyst at 40° C. that is greater by a factor of at least 7 than a partition coefficient for extraction of the formic acid present at a concentration of 5 wt % in water at 40° C., and where the extractant before the extraction is saturated with the catalyst or where the separated catalyst is separated from the extractant and resupplied to the liquid solution in the vessel.

15. The method as claimed in claim 14, characterized in that the separation takes place in a two-stage process, by extracting the liquid solution in a first extraction step with a first quantity of the extractant for a first time, to extract the catalyst, and extracting the solution in a second extraction step with a second quantity of the extractant for a second time, to extract the formic acid, where the catalyst extracted in the first extraction step is supplied again to the liquid solution in the vessel.

16. The method as claimed in claim 14, characterized in that the extractant is admixed with an additive.

17. The method as claimed in claim 14, characterized in that the extractant is an amide.

18. The method as claimed in claim 14, characterized in that the catalyst is separated by means of precipitation as a salt or by means of further extraction with a polar further extractant and with a temperature change of the extractant and/or an increase in the pH of the extractant.

19. The method of claim 4, wherein the temperature below 150° C.

20. The method of claim 5, wherein the pressure is at most 15 bar.

21. The method of claim 8, wherein the absorbent is a linear alcohol or an amide.

22. The method of claim 9, wherein the nozzle is a Venturi nozzle or a spraying nozzle.

23. The method of claim 12, wherein the gas is guided in the circuit without a pressure drop of more than 2.5 bar.

* * * * *